(12) United States Patent
Masuda

(10) Patent No.: US 8,894,583 B2
(45) Date of Patent: Nov. 25, 2014

(54) WAKEFULNESS LEVEL DETERMINATION DEVICE, WAKEFULNESS LEVEL DETERMINATION METHOD, AND COMPUTER READABLE STORAGE MEDIUM

(71) Applicant: Fujitsu Limited, Kawasaki (JP)

(72) Inventor: Yuta Masuda, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 13/854,396

(22) Filed: Apr. 1, 2013

(65) Prior Publication Data

US 2013/0218035 A1   Aug. 22, 2013

Related U.S. Application Data

(63) Continuation of application No. PCT/JP2010/069213, filed on Oct. 28, 2010.

(51) Int. Cl.
*A61B 5/0205* (2006.01)
*A61B 5/00* (2006.01)
*A61B 5/18* (2006.01)
*A61B 5/0245* (2006.01)

(52) U.S. Cl.
CPC ............ *A61B 5/0205* (2013.01); *A61B 5/4809* (2013.01); *A61B 5/18* (2013.01); *A61B 5/4806* (2013.01); *A61B 5/0245* (2013.01)
USPC ...................................................... 600/508

(58) Field of Classification Search
CPC ........................... A61B 5/4806; A61B 5/4809
USPC ............................................... 600/508–509
See application file for complete search history.

(56) References Cited

U.S. PATENT DOCUMENTS

2004/0243013 A1  12/2004  Kawachi et al.
2006/0025698 A1   2/2006  Nakagawa et al.
(Continued)

FOREIGN PATENT DOCUMENTS

JP     10-80405      3/1998
JP     2004-350773   12/2004
(Continued)

OTHER PUBLICATIONS

Yuta Masuda et al., "Improvement of drowsiness detection accuracy by discerning driver's grapple with drowsiness," Proceedings of the Engineering Sciences Society Conference of IEICE 2009, Sep. 1, 2009; p. 168.

(Continued)

*Primary Examiner* — Paula J Stice
(74) *Attorney, Agent, or Firm* — Staas & Halsey LLP

(57) ABSTRACT

A wakefulness level determination device includes a processor; and a memory. The processor executes: calculating a first feature value from a heartbeat signal of a subject; estimating, from the first feature value calculated at the calculating, a feature value of the subject when not fully awake on the basis of a correlation between a feature value of a heartbeat signal of a person fully waking and a feature value of a heartbeat signal of a person not fully waking; setting, as an index of a wakefulness level, a range from the first feature value calculated at the calculating to the feature value estimated at the estimating; calculating a second feature value from a heartbeat signal of the subject; and determining a wakefulness level of the subject by comparing the second feature value with the index of the wakefulness level that is set at the setting.

9 Claims, 12 Drawing Sheets

(56) References Cited

U.S. PATENT DOCUMENTS

2009/0275847 A1* 11/2009 Karasudani .................. 600/509
2009/0326399 A1* 12/2009 Barrero Batalloso
 et al. ............................ 600/509

FOREIGN PATENT DOCUMENTS

| JP | 2006-34803 | 2/2006 |
| JP | 2006-158733 | 6/2006 |
| JP | 2010-155072 | 7/2010 |
| WO | WO 2008/065724 A1 | 6/2008 |
| WO | 2009/134205 | 5/2009 |

OTHER PUBLICATIONS

Japanese Office Action mailed Jun. 3, 2014 in corresponding Japanese Patent Application No. 2012-540586.
International Search Report of Corresponding PCT Application PCT/JP2010/069213 mailed Nov. 30, 2010.
Yuta Masuda et al., "Improvement of drowsiness detection accuracy by discerning driver's grapple with drowsiness", Proceedings of the Engineering Sciences Society Conference of IEICE 2009, Sep. 1, 2009; p. 168.

* cited by examiner

WAKEFULNESS LEVEL DETERMINATION DEVICE, WAKEFULNESS LEVEL DETERMINATION METHOD, AND COMPUTER READABLE STORAGE MEDIUM

CROSS-REFERENCE TO RELATED APPLICATION

This application is a continuation of International Application No. PCT/JP2010/069213, filed on Oct. 28, 2010, the entire contents of which are incorporated herein by reference.

FIELD

The embodiments discussed herein are directed to a wakefulness level determination device, a wakefulness level determination method, and a computer readable storage medium.

BACKGROUND

There is a conventional technology that determines the wakefulness level of a subject by using biometric information on the subject so that there is no burden placed on the subject. By using this technology in vehicles, it is possible, for example, to determine the wakefulness level of a driver and to report any danger.

There is a technology, for example, that uses the maximum frequency and the maximum spectral density, both calculated from a subject's heartbeat signal, to determine the wakefulness level of the subject. With this technology, a scale is previously set that is the range over which the maximum frequency and the maximum spectral density vary between when a subject is fully awake and when a subject is not fully awake, i.e., from the state in which a subject feels no drowsiness to the state in which the subject feels drowsy. The maximum frequency and the maximum spectral density are calculated every time the subject's heartbeat signal is obtained and the obtained values are applied to the scale, thereby determining the wakefulness level of the subject in real time.

Furthermore, there is a technology, for example, that uses the heart rate and the blood pressure obtained when a subject is fully awake to determine the wakefulness level of the subject. With this technology, a scale is set for each subject by using, as a reference value, the heart rate and the blood pressure obtained when the subject is fully awake and applying the reference value to a previously set scale. Then, these values are applied to the scale every time the heart rate and the blood pressure of the subject are obtained, thereby determining a wakefulness level of the subject in real time.

Patent Document 1: International Publication Pamphlet No. WO 2008/65724

Patent Document 2: Japanese Laid-open Patent Publication No. 2006-34803

However, with the technologies described above, there is a problem in that it is difficult to determine the wakefulness level of a subject.

For example, with the conventional technology that uses heartbeat signals, in order to set the scale, there is a need to obtain both heartbeat signals obtained when a subject is fully awake and heartbeat signals obtained when the subject is not fully awake. However, in reality, it is difficult to obtain heartbeat signals when a subject is not fully awake. Consequently, setting the scale for each subject is not easy, and thus, in reality, determining a wakefulness level of the subject is difficult.

Furthermore, because the conventional technology that uses both heart rate and blood pressure does not use measured values that are obtained when a subject is not fully awake, the scale is set for each subject. However, because the biometric information that is used in this conventional technology is different from that used in the conventional technology that uses heartbeat signals, these technologies are not easily combined.

SUMMARY

According to an aspect of an embodiment, a wakefulness level determination device includes a processor; and a memory. The processor executes: calculating a first feature value from a heartbeat signal of a subject; estimating, from the first feature value calculated at the calculating, a feature value of the subject when not fully awake on the basis of a correlation between a feature value of a heartbeat signal of a person fully waking and a feature value of a heartbeat signal of a person not fully waking; setting, as an index of a wakefulness level, a range from the first feature value calculated at the calculating to the feature value estimated at the estimating; calculating a second feature value from a heartbeat signal of the subject; and determining a wakefulness level of the subject by comparing the second feature value calculated at the calculating with the index of the wakefulness level that is set at the setting.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

Preferred embodiments of the present invention will be explained with reference to accompanying drawings. The present invention is not limited to these embodiments. The embodiments can be appropriately used in combination as long as the processes do not conflict with each other.

[a] First Embodiment

Figure 1:
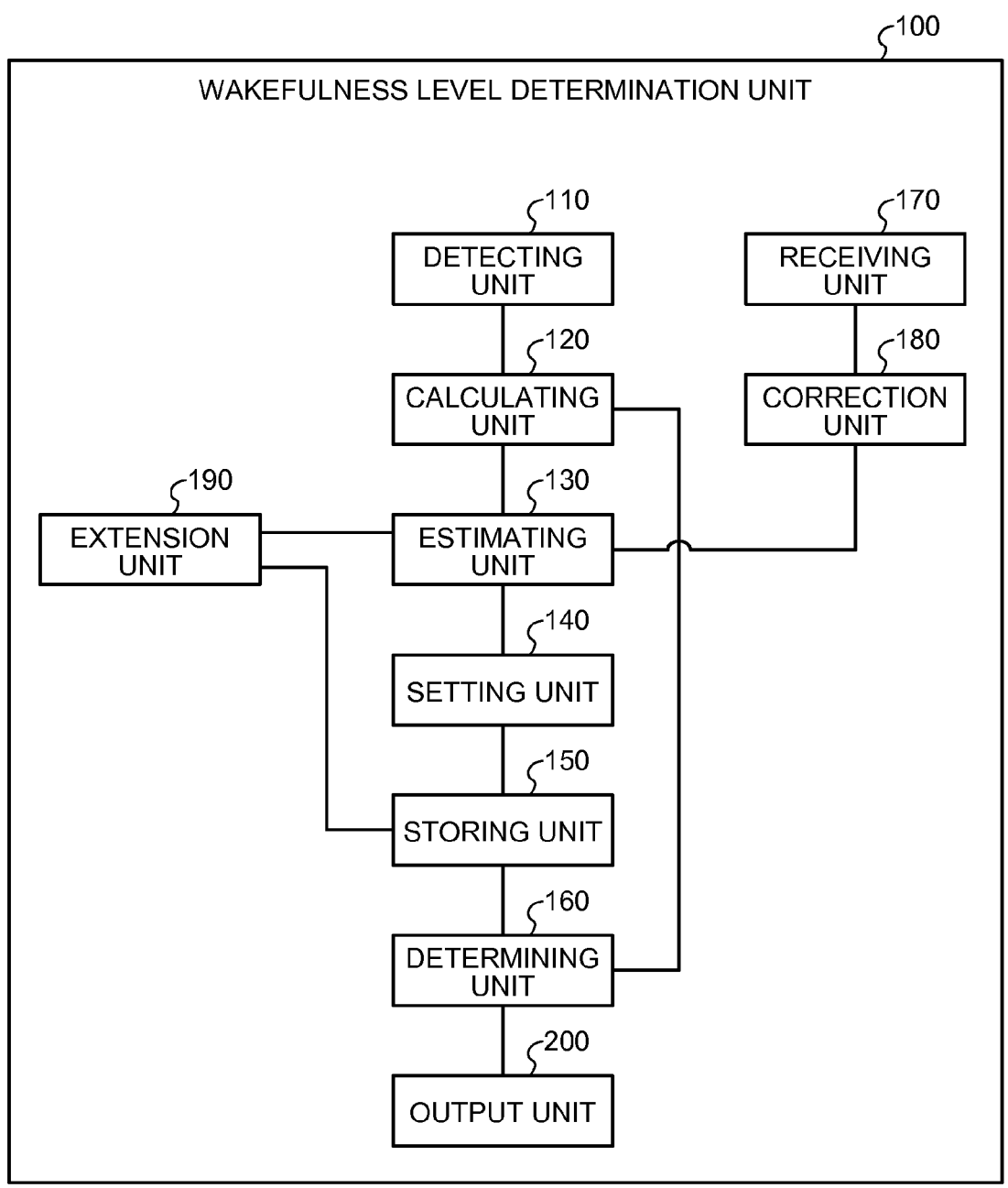
FIG. 1 is a schematic diagram illustrating the configuration of a wakefulness level determination unit according to a first embodiment.

An example of the configuration of a wakefulness level determination unit according to a first embodiment will be described here. FIG. 1 is a schematic diagram illustrating the configuration of a wakefulness level determination unit according to a first embodiment. As illustrated in FIG. 1, a wakefulness level determination unit 100 includes a detecting unit 110, a calculating unit 120, an estimating unit 130, a setting unit 140, a storing unit 150, a determining unit 160, a receiving unit 170, a correction unit 180, an extension unit 190, and an output unit 200.

The detecting unit 110 detects the heartbeat signal of a subject. For example, the detecting unit 110 applies a voltage to electrodes that are brought into close contact with a subject and obtains a heartbeat signal of the subject from the potential differences between the electrodes. The subject mentioned here corresponds to, for example, the driver of a vehicle. The electrodes that are used by the detecting unit 110 correspond to, for example, electrodes that are embedded in the steering wheel of the vehicle.

Figure 2:
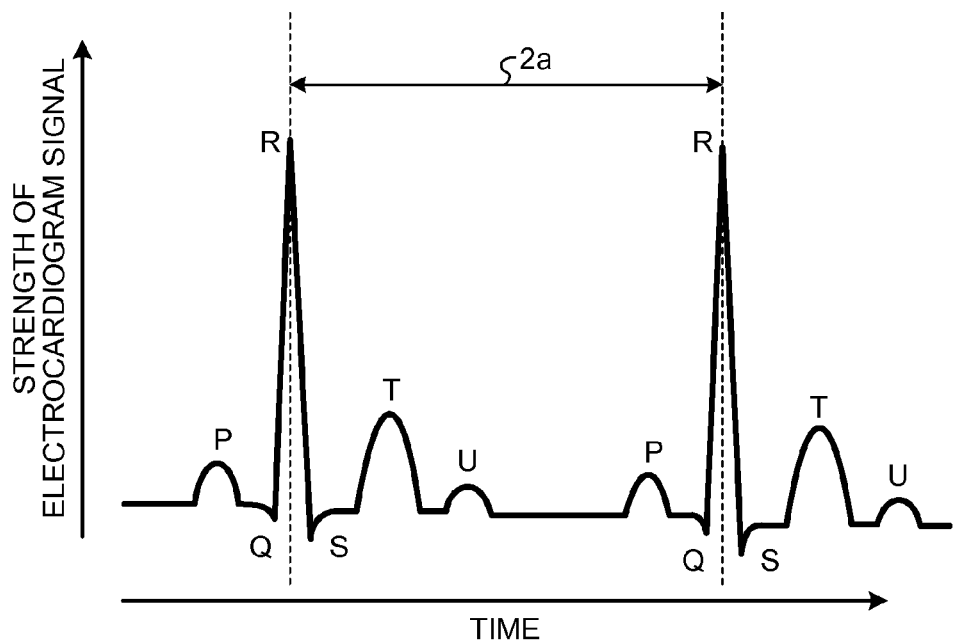
FIG. 2 is a schematic diagram illustrating an example of a heartbeat signal detected by a detecting unit.

FIG. 2 is a schematic diagram illustrating an example of a heartbeat signal detected by a detecting unit. In FIG. 2, the horizontal axis represents elapsed time and the vertical axis represents the strength of an electrocardiogram signal. As illustrated in FIG. 2, the electrocardiographic signal exhibited by a normal, healthy subject has, in general, four waveforms in time series and these waveforms are referred to as a P wave, a QRS wave, a T wave, and a U wave. In particular, the QRS wave is detected as a wave forming an acute angle and includes a Q wave that is the starting point of the peak, an R wave that corresponds to the peak, and an S wave that corresponds to the end point of the peak. A single waveform from the P wave to the U wave is associated with a single heartbeat. An R-R interval 2a, which is calculated as the interval between an R wave and the subsequent R wave, is associated with a heartbeat interval indicating the time intervals between successive heartbeats. The detecting unit 110 outputs, to the calculating unit 120, data on the detected heartbeat signal as heartbeat signal data.

The calculating unit 120 calculates a feature value from a subject's heartbeat signal. For example, on the basis of the heartbeat signal data received from the detecting unit 110, the calculating unit 120 obtains the maximum point of spectral density data and calculates, as feature values, the maximum frequency and the maximum spectral density of the obtained maximum point.

Figure 3:
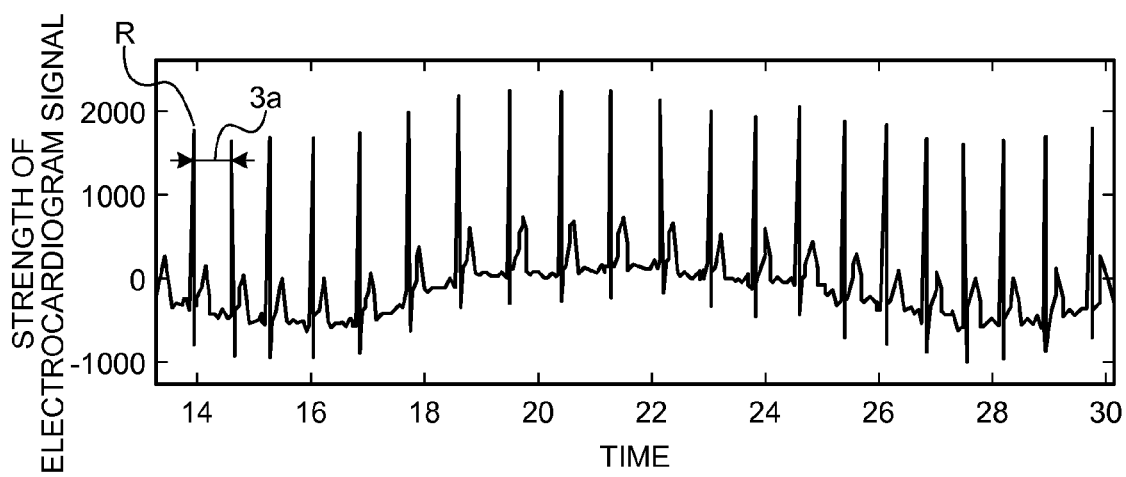
FIG. 3 is a schematic diagram illustrating a process in which a calculating unit calculates heartbeat intervals.

In the following, a process performed by the calculating unit 120 will be described in detail. The calculating unit 120 calculates a heartbeat interval from the heartbeat signal data received from the detecting unit 110. FIG. 3 is a schematic diagram illustrating a process in which a calculating unit calculates heartbeat intervals. In FIG. 3, the horizontal axis illustrated represents elapsed time and the vertical axis represents the intensity of electrocardiograph.

As illustrated in FIG. 3, the calculating unit 120 detects, as an R wave, the peak of the amplitude in which the amplitude of a heartbeat signal becomes equal to or greater than a threshold. Then, every time the calculating unit 120 detects an R wave, the calculating unit 120 calculates a heartbeat interval 3a from the time at which each R wave appears. The method of detecting the peak of the amplitude is not limited to the method described above. For example, the calculating unit 120 may also use a method that uses a zero crossing point in which the differential coefficient of a heartbeat signal changes from positive to negative or may also use a method that detects the peak of the amplitude by performing pattern matching on each amplitude waveform.

Figure 4:
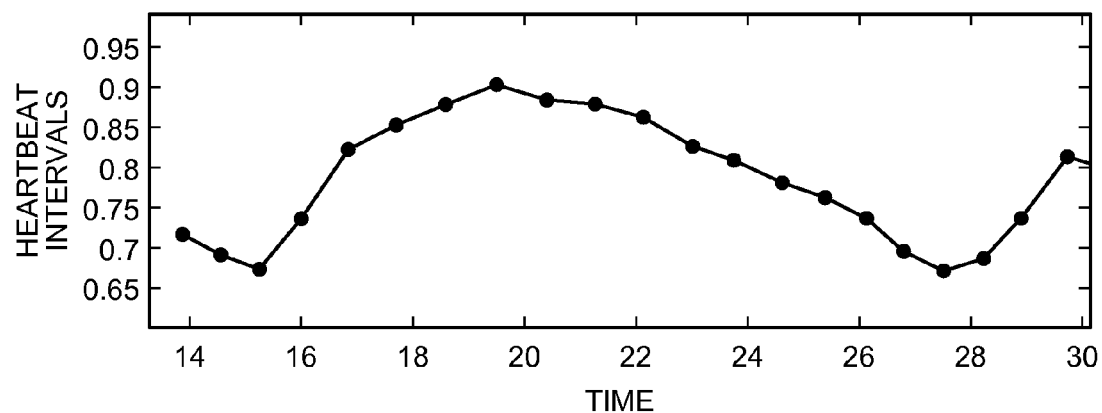
FIG. 4 is a graph illustrating an example of heartbeat interval variation data created by the calculating unit.

The calculating unit 120 creates, on the basis of the calculated heartbeat intervals, heartbeat interval variation data that indicates a variation in heartbeat intervals over time. FIG. 4 is a graph illustrating an example of heartbeat interval variation data created by the calculating unit. In FIG. 4, the horizontal axis represents elapsed time and the vertical axis represents the heartbeat intervals. As illustrated in FIG. 4, for example, the calculating unit 120 creates heartbeat interval variation data in which the calculated heartbeat intervals are associated with the detection time of the R waves.

The calculating unit 120 calculates, for each frequency, a spectral density by performing a frequency analysis on the heartbeat interval variation data. For example, the calculating unit 120 calculates a spectral density by using an Auto Regressive (AR) model. As disclosed in Non-Patent Document (Shunsuke Sato, Sho Kikkawa, and Toru Kiryu, "*Basic biological signal processing*", Corona publishing co., Ltd.), the AR model is a model in which a state at a certain time point is represented by the linear sum of time series data. The AR model has a feature in that a clear maximum point can be obtained even when the amount of data is small when compared with a Fourier transformation.

The AR model of order p in time series x(s) is represented by Equation (1) below:

$$x(s) = \sum_{m=1}^{p} a(m) \times (s-m) + e(s) \qquad (1)$$

where, a(m) represents an AR coefficient that is the weighting of the past value and e(s) represents an error term. Furthermore, ideally, e(s) represents white noise.

Then, if p represents an identification order, $f_s$ represents a sampling frequency, and $\epsilon_p$ represents an identification error, and Equation (2) below represents an AR coefficient of order k, the spectral density $P_{AR}(f)$ is represented by Equation (3) below:

$$\hat{a}_p(k) \qquad (2)$$

$$P_{AR}(f) = \frac{1}{f_s} \frac{\varepsilon_p}{\left|1 + \sum_{k=1}^{p} \hat{a}_p(k) e^{-2\pi jkf/f_s}\right|^2} \qquad (3)$$

The calculating unit 120 calculates a spectral density using Equation (3) and the heartbeat interval variation data. However, a method of calculating a spectral density is not limited to the above method. For example, the calculating unit 120 may also calculate a spectral density by using a Fourier transformation.

Figure 5:
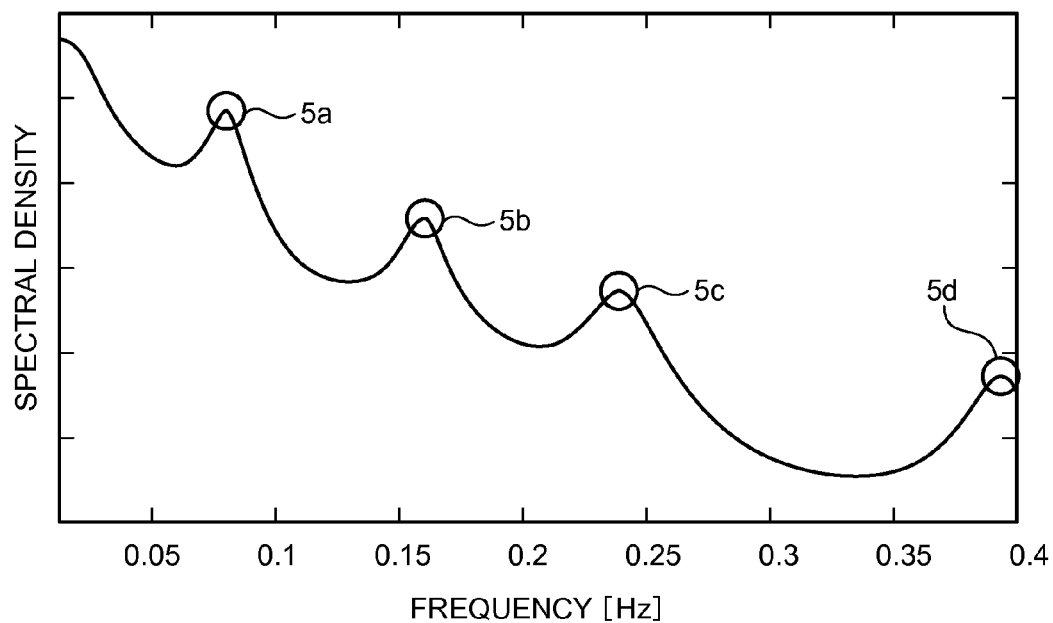
FIG. 5 is a graph illustrating an example of spectral density data created by the calculating unit.

Every time the calculating unit 120 calculates a spectral density, the calculating unit 120 creates spectral density data that indicates, for each frequency, the spectral density. FIG. 5 is a graph illustrating an example of spectral density data created by the calculating unit. In FIG. 5, the horizontal axis represents the frequency and the vertical axis represents the spectral density. For example, the components of the spectral densities appearing in the area between 0.05 and 0.15 Hz are Low Frequency (LF) components, which indicate an active state of the sympathetic nerve. Furthermore, for example, the components of the spectral densities appearing in the area between 0.15 and 0.4 Hz are High Frequency (HF) components, which indicate an active state of the parasympathetic nerve.

The calculating unit 120 obtains the maximum point at which the spectral density of the spectral density data becomes the maximum. For example, the calculating unit 120 calculates a frequency f by using Equation (4) below as the frequency of the maximum point and substitutes the frequency of this maximum point into Equation (3) to calculate the spectral density of the maximum point.

$$\frac{dP_{AR}(f)}{df} = 0 \quad (4)$$

In the example illustrated in FIG. 5, the calculating unit 120 acquires four maximum points 5a, 5b, 5c, and 5d. In the description below, the frequency of the maximum point is represented by "the maximum frequency" and the spectral density of the maximum point is represented by "the maximum spectral density".

From among the obtained maximum points of 5a, 5b, 5c, and 5d, the calculating unit 120 selects a single maximum point that is contained in the obtained HF component. As illustrated in FIG. 5, if multiple maximum points are contained in the HF component, the calculating unit 120 selects a maximum point 5b having the lowest frequency. The reason for this is because, from among the maximum points contained in the HF component, the maximum point on the low frequency side indicates a breathing state. In contrast, although the maximum point on the high frequency side indicates breathing, it is affected by a factor other than the breathing, such as body motion. In general, when a subject is not fully awake, i.e., a subject is feeling strong drowsiness, the subject's breathing is soft; therefore, it is assumed that the drowsiness of the subject can be more accurately determined by selecting the maximum point contained in the component that clearly indicates a breathing state. If the maximum point is not contained in the HF component, the calculating unit 120 selects a single maximum point having the lowest frequency in the area on the side in which the frequency is higher than 0.4 Hz. Furthermore, if a single maximum point is contained in the HF component, the calculating unit 120 selects the corresponding maximum point.

Figure 6:
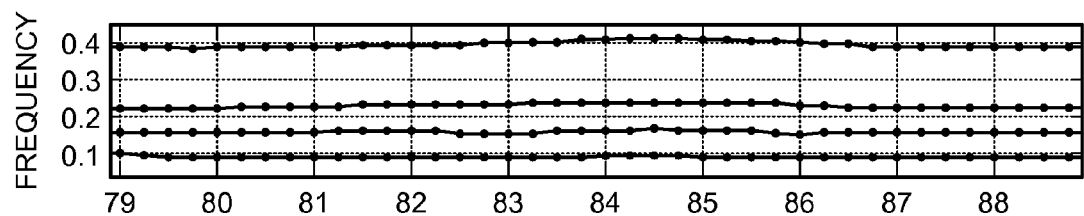
FIG. 6 is a graph illustrating the maximum frequency in time series.
Figure 7:
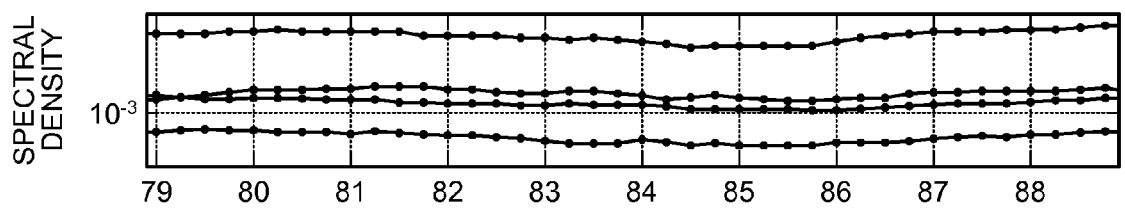
FIG. 7 is a graph illustrating the maximum spectral density represented in time series.

The calculating unit 120 calculates the maximum frequency and the maximum spectral density of the obtained maximum point. FIG. 6 is a graph illustrating the maximum frequency in time series. In FIG. 6, the horizontal axis represents elapsed time and the vertical axis represents the frequency. FIG. 7 is a graph illustrating the maximum spectral density represented in time series. In FIG. 7, the horizontal axis represents elapsed time and vertical axis represents the spectral density. If the calculating unit 120 calculates spectral density data at intervals of 10 seconds, the intervals represented by dots in the time series direction illustrated in FIGS. 6 and 7 are 10-second intervals. As illustrated in FIGS. 6 and 7, the calculating unit 120 calculates the maximum frequency and the maximum spectral density for every certain time period.

A description will be given here by referring back to FIG. 1. On the basis of the correlation between a feature value of a subject when fully awake and a feature value of a subject when not fully awake, the estimating unit 130 estimates a feature value of a subject when not fully awake from the feature value calculated by the calculating unit 120. For example, by using the correlation between the maximum frequency and the maximum spectral density of a subject when fully awake and when not fully awake, the estimating unit 130 estimates a feature value of a subject when not fully awake from values obtained during the few minutes after driving has started. The reason for using the values obtained during the few minutes after the driving has started is because a driver is supposedly fully awake for the few minutes after the start of driving, a feature value of a subject when fully awake can be reliably obtained.

Figure 8:
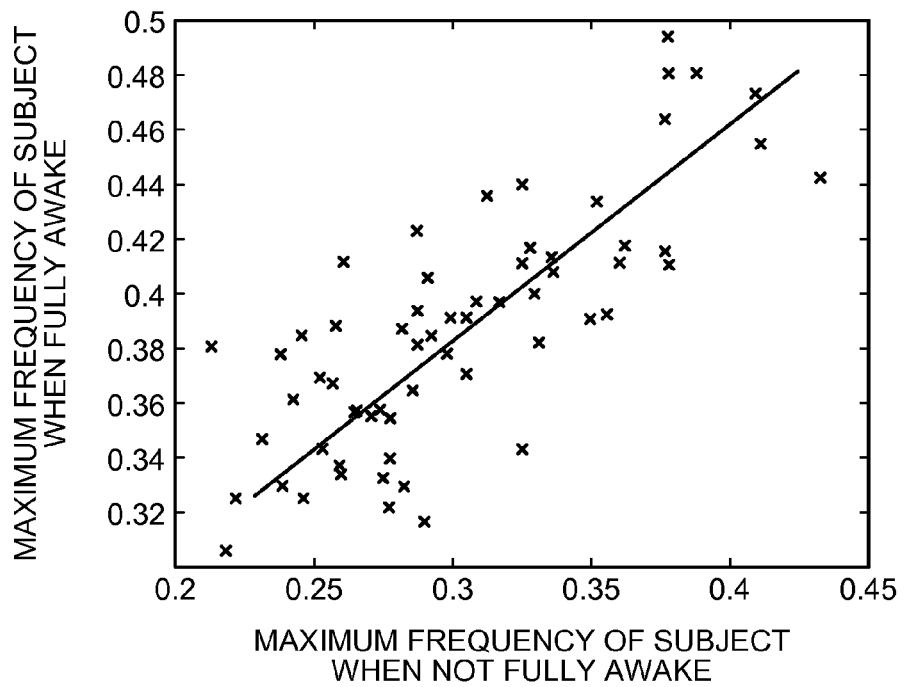
FIG. 8 is a graph illustrating the correlation between the maximum frequency of a subject when fully awake and the maximum frequency when not fully awake.
Figure 9:
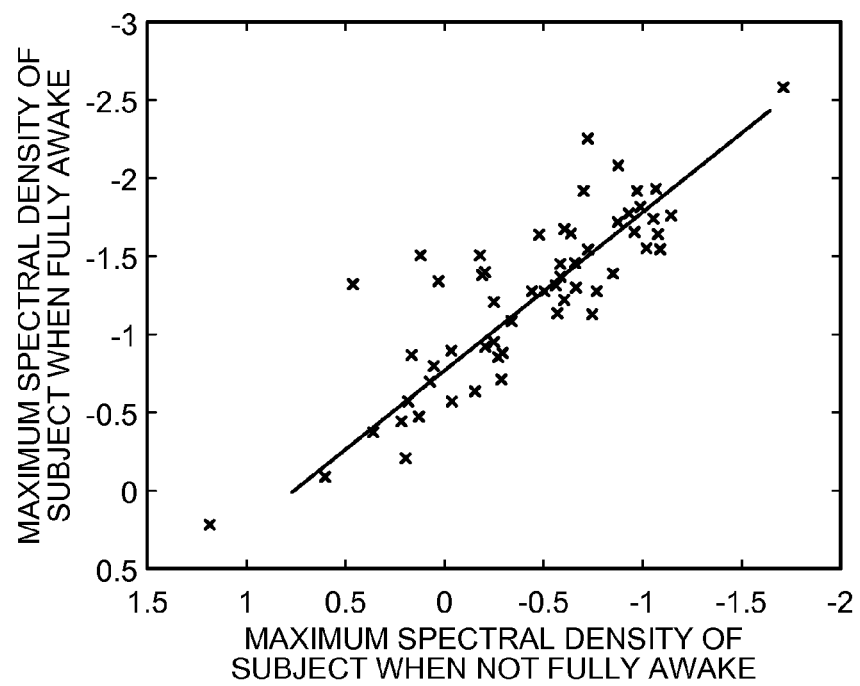
FIG. 9 is a graph illustrating the correlation between the maximum spectral density of a subject when fully awake and the maximum spectral density when not fully awake.

In the following, the correlation used by the estimating unit 130 will be described. FIG. 8 is a graph illustrating the correlation between the maximum frequency of a subject when fully awake and the maximum frequency when not fully awake. In FIG. 8, the horizontal axis represents the maximum frequency of a subject when not fully awake and the vertical axis represents the maximum frequency of a subject when fully awake. FIG. 9 is a graph illustrating the correlation between the maximum spectral density of a subject when fully awake and the maximum spectral density when not fully awake. In FIG. 9, the horizontal axis represents the maximum spectral density of a subject when not fully awake and the vertical axis represents the maximum spectral density of a subject when fully awake.

FIGS. 8 and 9 each illustrates an example of the result of experiments in which a heartbeat signal of each subject is obtained by using a driving simulator. As illustrated in FIGS. 8 and 9, when values of a subject when fully awake and when not fully awake are plotted, a regression line is obtained. The result of the experiments indicates that the maximum frequency correlates with the maximum spectral density when a subject is fully awake and when a subject is not fully awake. In the examples illustrated in FIGS. 8 and 9, the correlation coefficient of the maximum frequency is 0.78 and the correlation coefficient of the maximum spectral density is 0.85, respectively.

For example, the estimating unit 130 obtains the maximum frequency and the maximum spectral density from the calculating unit 120. If a scale of a subject is not set, the estimating unit 130 sets the obtained maximum frequency and the maximum spectral density as the reference point. By substituting the maximum frequency and the maximum spectral density of the set reference point into an equation of the regression line illustrated in FIGS. 8 and 9, the estimating unit 130 calculates the maximum frequency and the maximum spectral density of a subject when not fully awake. Then, the estimating unit 130 uses the calculated maximum frequency and the maximum spectral density of the subject when not fully awake as an estimation point and outputs both the reference point and the estimation point to the setting unit 140. In contrast, if a scale of a subject is set, the estimating unit 130 outputs the obtained maximum frequency and the maximum spectral density to the extension unit 190.

Furthermore, if the reference point is corrected by the correction unit 180, which will be described later, the estimating unit 130 estimates a point (hereinafter, referred to as an estimation point) by using the corrected reference point, which will be described later. Then, the estimating unit 130 outputs both the reference point and the estimation point to the setting unit 140.

The setting unit 140 sets, as the index of a wakefulness level, the range from the feature value calculated by the calculating unit 120 to the feature value estimated by the estimating unit 130. For example, the setting unit 140 sets, as a scale corresponding to the index of a wakefulness level, the range over which the frequency and the spectral density are likely to vary between the reference point and the estimation point.

Figure 10:
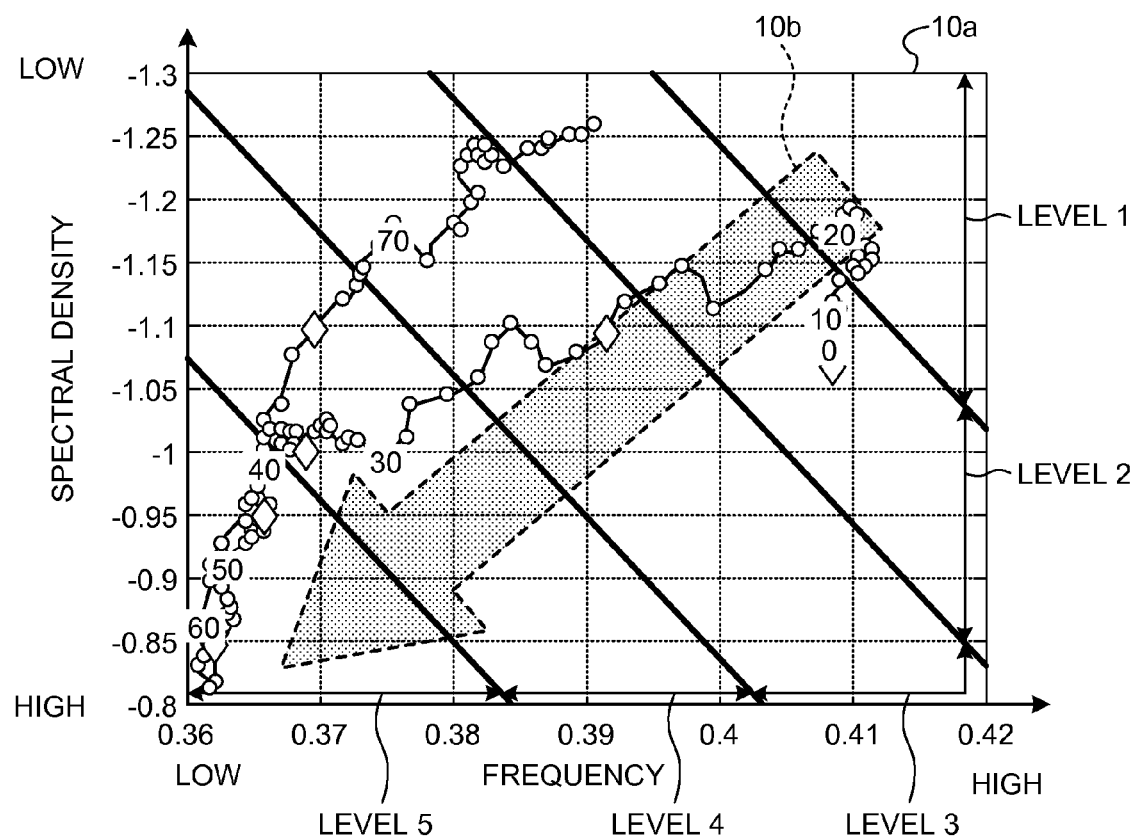
FIG. 10 is a graph illustrating an example of a scale that is set by a setting unit.

In the following, a scale that is set by the setting unit 140 will be described. FIG. 10 is a graph illustrating an example of a scale that is set by a setting unit. In FIG. 10, the horizontal axis represents the frequency and the vertical axis represents the spectral density. In the example illustrated in FIG. 10, as indicated by a drowsiness direction 10b, a scale 10a is set such that drowsiness is weaker at the upper right of the graph and drowsiness is stronger at the lower left of the graph. In this case, the scale 10a is divided into five areas from the upper right to the lower left and five drowsiness levels are allocated to the five areas, respectively. Specifically, the drowsiness levels determined by the scale 10a are set such that drowsiness is stronger and the wakefulness level becomes lower from level 1 toward level 5. As illustrated in FIG. 10, the setting unit 140 has a normalized scale 10a. Data on the scale that is set by the setting unit 140 is data that contains, for example, an equation indicating the boundary of the areas in a scale and values of the drowsiness levels. In FIG. 10, a description has been given of a case in which the width of each area of the normalized scale 10a has the same intervals; however, the configuration is not limited thereto. For example, the width of each area of the normalized scale 10a may also be set such that the width is narrower as the drowsiness level becomes higher. Furthermore, the data on the scale is not limited to the above configuration. For example, the data may also contain the frequency and the spectral density of the reference point and that of the estimation point.

Figure 11:
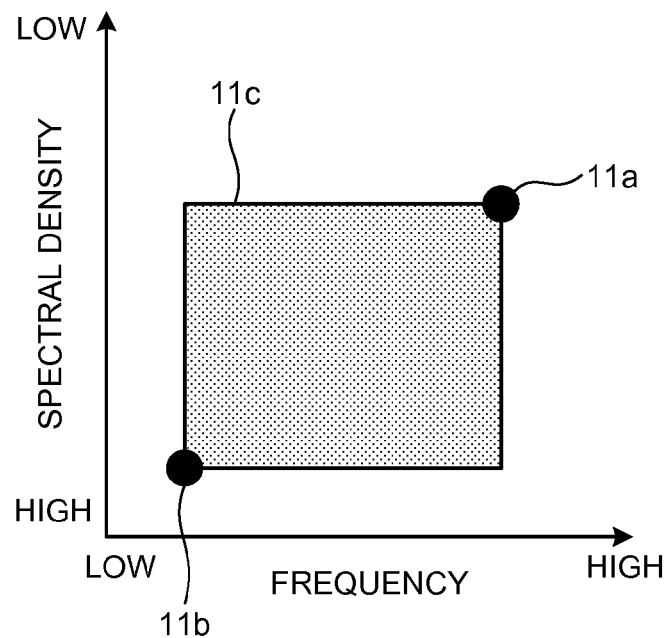
FIG. 11 is a schematic diagram illustrating a process in which a setting unit sets a scale.

In the following, a process in which the setting unit 140 sets a scale will be described. FIG. 11 is a schematic diagram illustrating a process in which a setting unit sets a scale. In FIG. 11, the horizontal axis represents the frequency and the vertical axis represents the spectral density. As illustrated in FIG. 11, the setting unit 140 sets the normalized scale 10a by using the value of the reference point and the value of the estimation point. For example, the setting unit 140 associates the frequency of the reference point with the maximum value of the frequency of the normalized scale 10a. The setting unit 140 associates the spectral density of the reference point with the minimum value of the spectral density of the normalized scale 10a. The setting unit 140 associates the frequency of the estimation point with the minimum value of the frequency of the normalized scale 10a. The setting unit 140 associates the spectral density of the estimation point with the maximum value of the spectral density of the normalized scale 10a. The setting unit 140 divides the associated scale 10a into five and sets areas that are associated with drowsiness levels. The setting unit 140 performs a calculation by using an equation indicating the boundary of each set area of the scale 10a and thereby a scale 11c for a subject is set. Then, the setting unit 140 stores the set scale in the storing unit 150.

A description will be given here by referring back to FIG. 1. The storing unit 150 stores therein the index of a wakefulness level that is set by the setting unit 140. For example, the storing unit 150 stores therein the scale of a subject that is set by the setting unit 140 by associating it with identification information that identifies the subject.

The determining unit 160 compares the feature value calculated by the calculating unit 120 with the index of the wakefulness level that is set by the setting unit 140 and determines the wakefulness level of a subject. For example, the determining unit 160 receives an input of the identification information on a subject and reads a scale that is associated with the identification information from the storing unit 150. The determining unit 160 then determines which area of a scale contains the maximum point that is calculated by the calculating unit 120. Specifically, for example, by substituting the maximum frequency and the maximum spectral density of the maximum point into the equation representing each area of the scale, the determining unit 160 determines an area that contains the calculated maximum point. The determining unit 160 determines the drowsiness level of a subject in accordance with the area that contains the maximum point. Then, the determining unit 160 outputs the determination result to the output unit 200. However, the method of receiving the identification information is not limited to the method described above. For example, the determining unit 160 may also use a method that obtains identification information from an image of the current subject captured by a camera or a method that determines whether identification information is received by using an area that is featured in a subject indicated by the heartbeat signals.

The receiving unit 170 receives, from a subject, an instruction to correct the feature value that is calculated by the calculating unit 120. For example, the receiving unit 170 corresponds to a touch panel. For example, if the estimating unit 130 sets a reference point, the receiving unit 170 queries a subject about the current drowsiness level. Then, if the current drowsiness level received from a subject is not "1", the receiving unit 170 outputs the current drowsiness level received from the subject to the correction unit 180. In contrast, if the current drowsiness level received from a subject is "1" or the current drowsiness level is not received from a subject within a predetermined time period, the receiving unit 170 ends the process and waits until the estimating unit 130 sets a reference point again.

The correction unit 180 corrects, on the basis of the instruction received by the receiving unit 170, the feature value that is the reference of the index of the wakefulness level. For example, by adding, in accordance with the current drowsiness level of a subject received from the receiving unit 170, a predetermined value to each of the maximum frequency and the maximum spectral density of the reference point that is set by the estimating unit 130, the correction unit 180 moves the reference point. Then, the correction unit 180 sets the moved reference point as the corrected reference point. At this point, the predetermined value that is added to the maximum frequency is, for example, "0.02" and the predetermined value that is added to the maximum spectral density is, for example, "−0.2". However, the predetermined value is not limited to the value in the example described above. For example, a person who uses the wakefulness level determination unit 100 may set an arbitrary value in accordance with the current drowsiness level of a subject.

Figure 12:
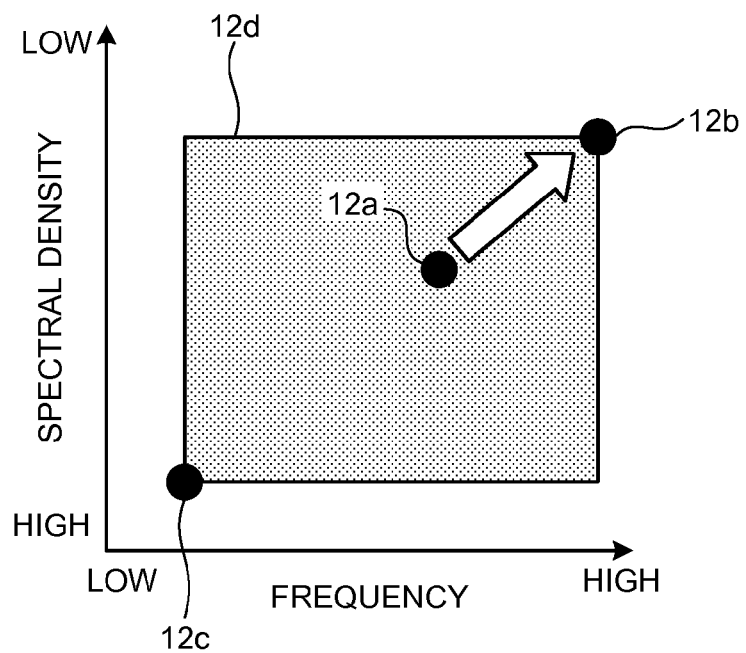
FIG. 12 is a schematic diagram illustrating a process in which a correction unit corrects a reference point.

FIG. 12 is a schematic diagram illustrating a process in which a correction unit corrects a reference point. In FIG. 12, the horizontal axis represents the frequency and the vertical axis represents the spectral density. As illustrated in FIG. 12, if the current drowsiness level of a subject is, for example, "2", the correction unit 180 adds "0.02" to the maximum frequency of the reference point 12a and adds "−0.2" to the maximum spectral density, thus moving the reference point 12a to a reference point 12b. Then, the correction unit 180 sets the reference point 12b as the corrected reference point. The estimation point that is estimated on the basis of the reference point 12b is an estimation point 12c. Furthermore, the scale that is set on the basis of the reference point 12b and the estimation point 12c is a scale 12d.

The reason for the correction unit 180 correcting the reference point is because, although a reference point is set by using the feature value when the drowsiness level of a subject is "1", the drowsiness level of the subject at this point is not always "1". For example, if a subject starts driving when the subject is already feeling drowsy, the estimating unit 130 erroneously set, as a reference point, the maximum frequency and the maximum spectral density calculated when the drowsiness level is not "1", and furthermore, estimates an estimation point by using an incorrect reference point. Consequently, in order to accurately estimate an estimation point, by receiving the current drowsiness level of the subject from the receiving unit 170, the correction unit 180 corrects the reference point that is erroneously set.

If the feature value calculated by the calculating unit 120 is outside the index range of the wakefulness level, the extension unit 190 extends the index of the wakefulness level. For example, when the extension unit 190 obtains, from the estimating unit 130, the maximum frequency and the maximum spectral density calculated by the calculating unit 120, the extension unit 190 determines whether the obtained value is outside the scale of the subject stored in the storing unit 150.

If the obtained value is outside the scale, the extension unit 190 determines whether the distance between the obtained value and the scale is equal to or greater than a threshold. If the distance is not equal to or greater than the threshold, the extension unit 190 extends the scale of the subject and stores the extended scale in the storing unit 150. In contrast, if the distance is equal to or greater than the threshold, the extension unit 190 waits until the maximum frequency and the maximum spectral density are obtained again. The threshold used at this point is a value for excluding an error when a heartbeat signal is analyzed. The threshold is set to, for example, 0.1 for a value of the maximum frequency. The reason for this is because, if a difference between a value of the maximum frequency and a scale is equal to or greater than 0.1, it is determined that a different maximum point has been detected. However, the threshold is not limited to the example described above. For example, a person that uses the wakefulness level determination unit 100 may also arbitrarily set a value.

Figure 13:
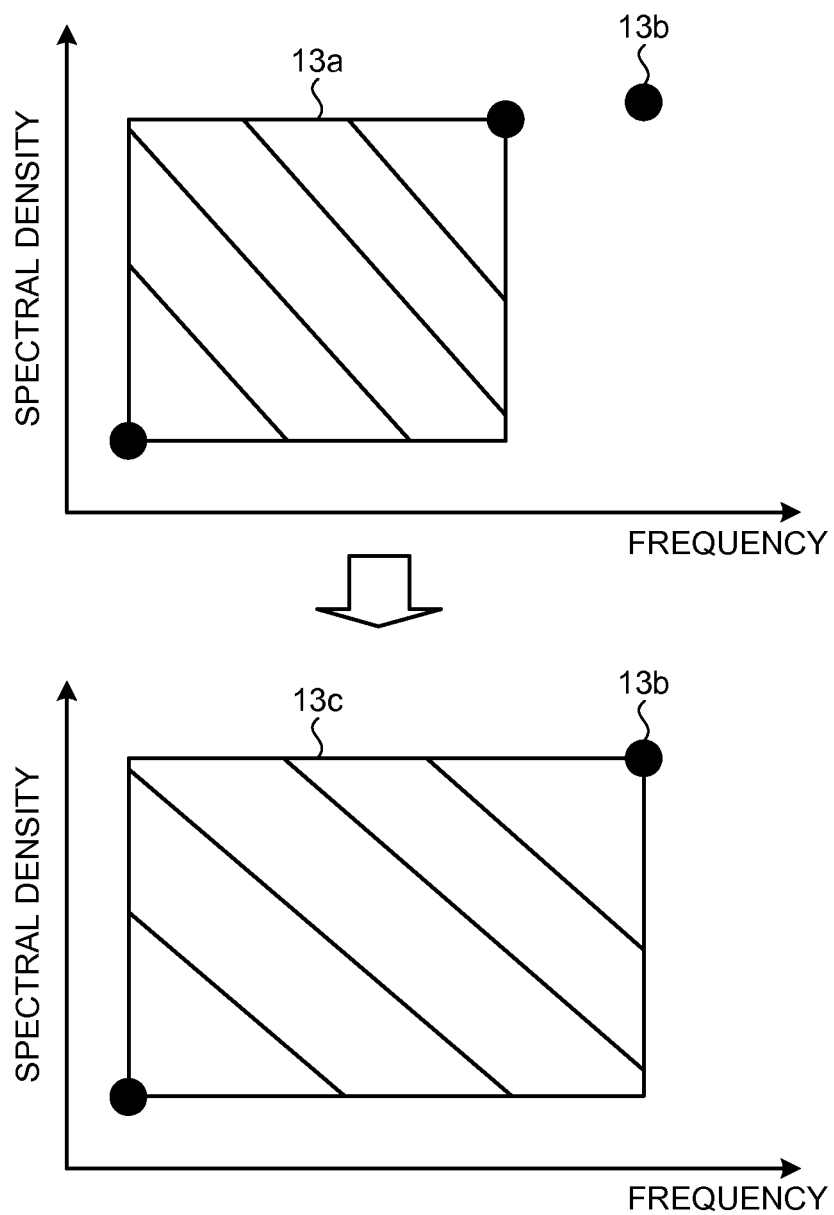
FIG. 13 is a schematic diagram illustrating a process in which an extension unit extends all of a scale.

In the following, a process in which an extension unit 190 extends a scale will be described. For example, the extension unit 190 moves each side of a scale such that a previously set scale includes values that are outside the scale. Then, by applying each side to the normalized scale and by setting a scale, the extension unit 190 extends the entire scale. FIG. 13 is a schematic diagram illustrating a process in which an extension unit extends the entire scale. In FIG. 13, the horizontal axis represents the frequency and the vertical axis represents the spectral density. As illustrated in FIG. 13, the extension unit 190 moves both the upper side and the right side of a scale 13a such that a previously set scale 13a includes a value 13b outside the scale. Then, by applying each side to the normalized scale and by setting a scale 13c, the extension unit 190 extends the entirety of the scale 13a.

Figure 14:
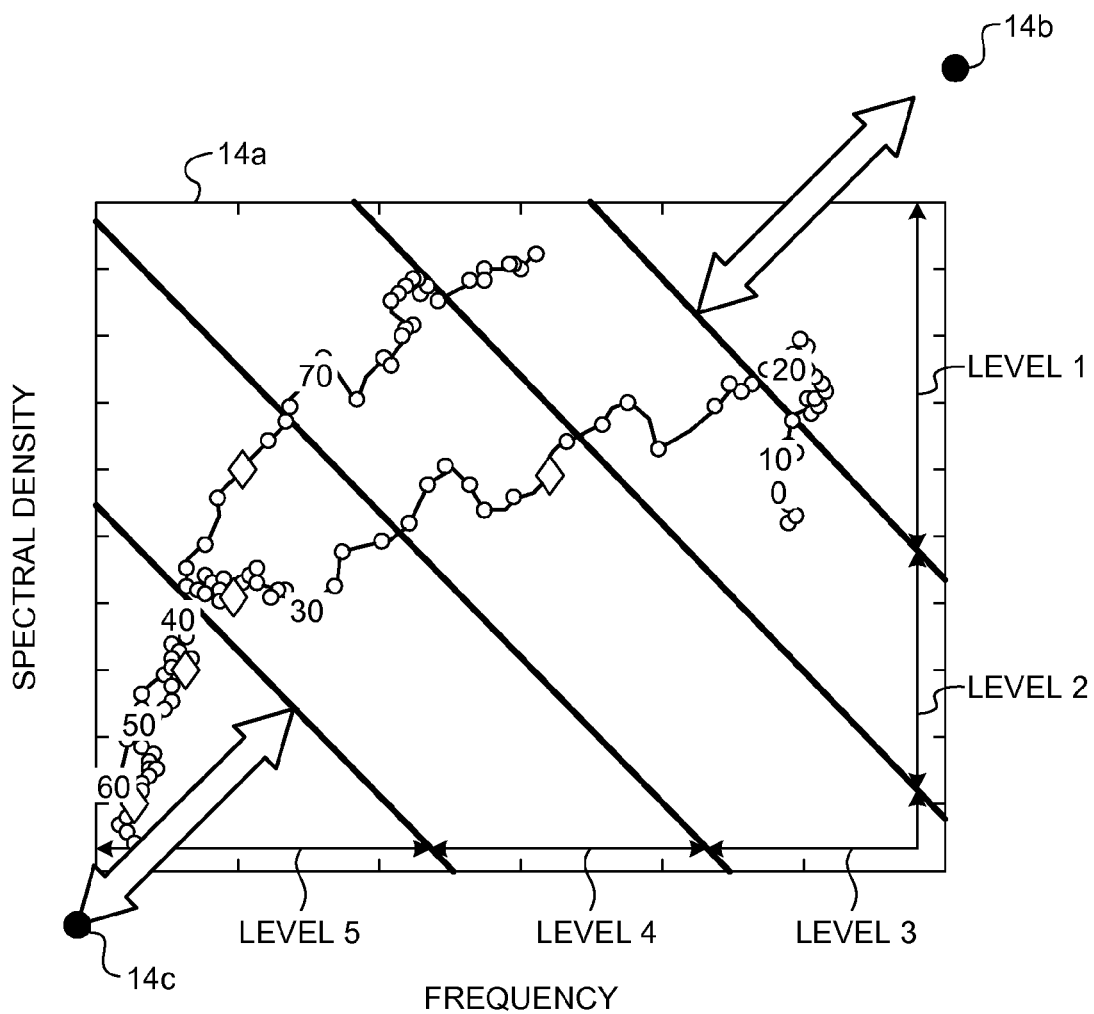
FIG. 14 is a schematic diagram illustrating a process in which the extension unit partially extends a scale.

Furthermore, for example, the extension unit 190 partially extends only an area close to outside the scale in a previously set scale. FIG. 14 is a schematic diagram illustrating a process in which the extension unit partially extends a scale. In FIG. 14, the horizontal axis represents the frequency and the vertical axis represents the spectral density. As illustrated in FIG. 14, if a value 14b is present, for example, outside the right side of a scale 14a in the upward direction, the extension unit 190 extends, with respect to the value 14b outside the scale, only the area of the level 1. Furthermore, if a value 14c is present, for example, outside the right side of the scale 14a in the downward direction, the extension unit 190 extends, with respect to the value 14c outside the scale, only the area of the level 5.

The reason that the extension unit 190 extends a scale is that, if the maximum frequency and the maximum spectral density calculated by the calculating unit 120 are outside the scale, the determining unit 160 does not determine a drowsiness level. Consequently, even if the calculated the maximum frequency and the maximum spectral density are outside the scale, the extension unit 190 extends the scale in order to determine the calculated drowsiness level.

The output unit 200 outputs the determination result that is determined by the determining unit 160. The output unit 200 corresponds to, for example, a monitor or a speaker. For example, the output unit 200 reports, to a subject or a person near the subject, information indicating that the wakefulness level of the subject has become low.

Figure 15:
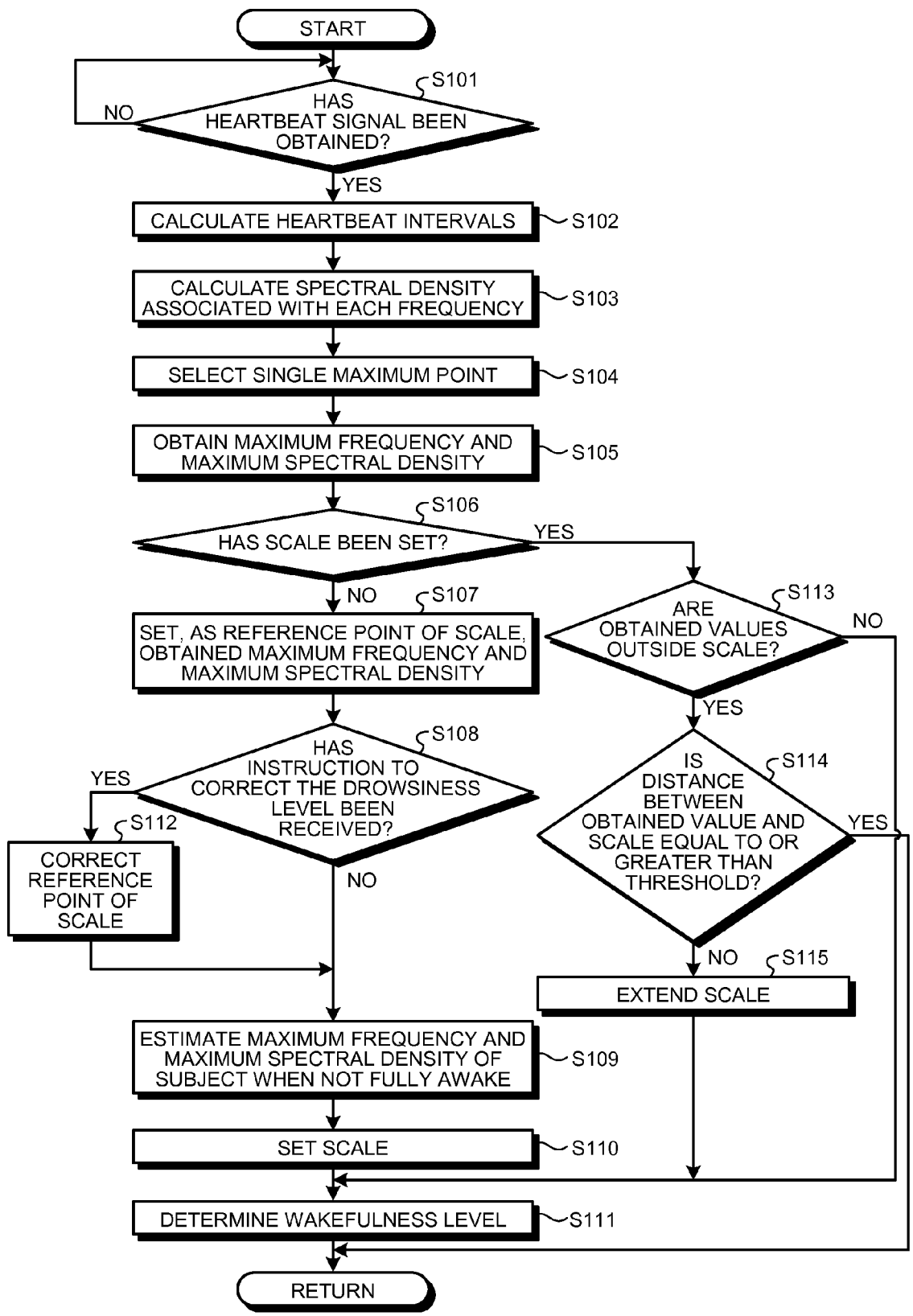
FIG. 15 is a flowchart illustrating the flow of a process performed by a wakefulness level determination unit according to the first embodiment.

In the following, the flow of a process performed by the wakefulness level determination unit 100 according to the first embodiment will be described. FIG. 15 is a flowchart illustrating the flow of a process performed by a wakefulness level determination unit according to the first embodiment. The process illustrated in FIG. 15 is performed when, for example, a vehicle-mounted system that includes the wakefulness level determination unit 100 is booted up.

As illustrated in FIG. 15, if the detecting unit 110 obtains heartbeat signal data on a subject (Yes at Step S101), the calculating unit 120 calculates heartbeat intervals (Step S102). The calculating unit 120 calculates, on the basis of the calculated heartbeat intervals, the spectral density associated with each frequency (Step S103). Specifically, on the basis of the calculated heartbeat intervals, the calculating unit 120 creates heartbeat interval variation data indicating a variation in heartbeat intervals over time and performs a frequency analysis on the heartbeat interval variation data, thereby calculating the spectral density for each frequency.

The calculating unit 120 selects a single maximum point contained in the HF component from among the maximum points having the maximum spectral density (Step S104). Specifically, every time the calculating unit 120 calculates a spectral density, the calculating unit 120 creates spectral density data that indicates a spectral density for each frequency and selects, from among the maximum points having the maximum spectral density stored in the spectral density data, a single maximum point contained in the HF component.

The estimating unit 130 obtains, from the calculating unit 120, the maximum frequency and the maximum spectral density of the maximum point selected by the calculating unit 120 (Step S105). Then, if a scale of a subject has not been set (No at Step S106), the estimating unit 130 sets, as a reference point of a scale, the obtained maximum frequency and the maximum spectral density (Step S107).

If the estimating unit 130 does not receive an instruction to correct the drowsiness level from a subject (No at Step S108), the estimating unit 130 estimates the maximum frequency and the maximum spectral density of a subject when not fully awake (Step S109). Specifically, if the current drowsiness level received by the receiving unit 170 from a subject is "1" or if the receiving unit 170 does not receive the current drowsiness level from a subject within a predetermined time period, by substituting a value of the set reference point into an equation of a regression line, the estimating unit 130 calculates a value of a subject when not fully awake and defines the calculated value as an estimation point. Then, the estimating unit 130 outputs both the reference point and the estimation point to the setting unit 140.

On the basis of the reference point and the estimation point received from the estimating unit 130, the setting unit 140 sets a scale (Step S110). Specifically, from the maximum frequency and the maximum spectral density of a reference point 11a and an estimation point 11b received from the estimating unit 130, the setting unit 140 calculates the amount of variation in the frequency and the spectral density from when a subject is fully awake toward when a subject is not fully awake. The setting unit 140 associates the calculated amount of variation of frequency and the spectral density with the normalized scale 10a, thereby setting a scale of the subject. Then, the setting unit 140 stores the set scale in the storing unit 150.

By comparing the scale with the maximum frequency and the maximum spectral density calculated by the calculating unit 120, the determining unit 160 determines the wakefulness level of the subject (Step S111). Specifically, the determining unit 160 determines the drowsiness level of the subject in accordance with the area of the scale that contains the maximum frequency and the maximum spectral density calculated by the calculating unit 120.

In contrast, if the estimating unit 130 receives an instruction to correct the drowsiness level from a subject (Yes at Step S108), the estimating unit 130 corrects the reference point of the scale (Step S112) and moves to Step S109. Specifically, in accordance with the current drowsiness level of the subject received from the receiving unit 170, the correction unit 180 adds a predetermined value to each of the maximum frequency and the maximum spectral density of the reference point that is set by the estimating unit 130, thereby moving the reference point. Then, the correction unit 180 sets the moved reference point as the corrected reference point.

In contrast, if a scale of a subject has been set (Yes at Step S106), the estimating unit 130 outputs the obtained maximum frequency and the maximum spectral density to the extension unit 190.

When the extension unit 190 obtains the maximum frequency and the maximum spectral density calculated by the calculating unit 120 from the estimating unit 130, the extension unit 190 determines whether the obtained values are outside the scale of the subject stored in the storing unit 150 (Step S113). If the obtained value is outside the scale (Yes at Step S113), the extension unit 190 determines whether the distance between the obtained value and the scale is equal to or greater than a threshold (Step S114). If the distance is not equal to or greater than the threshold (No at Step S114), the extension unit 190 extends the scale of the subject (Step S115) and moves to Step S111.

In contrast, if the distance is equal to or greater than the threshold (Yes at Step S114), the extension unit 190 ends the process and wait until the maximum frequency and the maximum spectral density are obtained again.

In contrast, if the obtained value is not outside the scale (No at Step S113), the extension unit 190 ends the process and moves to Step S111.

From among the processes described above, it is not always need to perform the processes that are performed at Steps S108 and S112 and that correct the reference point. Specifically, after the process at Step S107 is performed, the process at Step S109 may also be performed.

Furthermore, from among the processes described above, it is not always need to perform the processes that are performed at Steps S113 to S115 and that extends a scale. Specifically, if it is determined that, at the process at Step S106, a scale is set, the process at Step S111 may also be performed.

In the following, an effect of the wakefulness level determination unit 100 according to the first embodiment will be described. The wakefulness level determination unit 100 according to the first embodiment creates spectral density data on the basis of the heartbeat signal of a subject and obtains the maximum point from the HF component of the created spectral density data. Then, by using the correlation between the maximum frequency and the maximum spectral density of the maximum point of a subject when fully awake and when not fully awake, the wakefulness level determination unit 100 estimates a value of a subject when not fully awake from a value of the subject when fully awake, thus easily setting a scale. Consequently, the wakefulness level determination unit 100 can determine the wakefulness level of a subject without previously obtaining the heartbeat signal of a subject when not fully awake.

Figure 16:
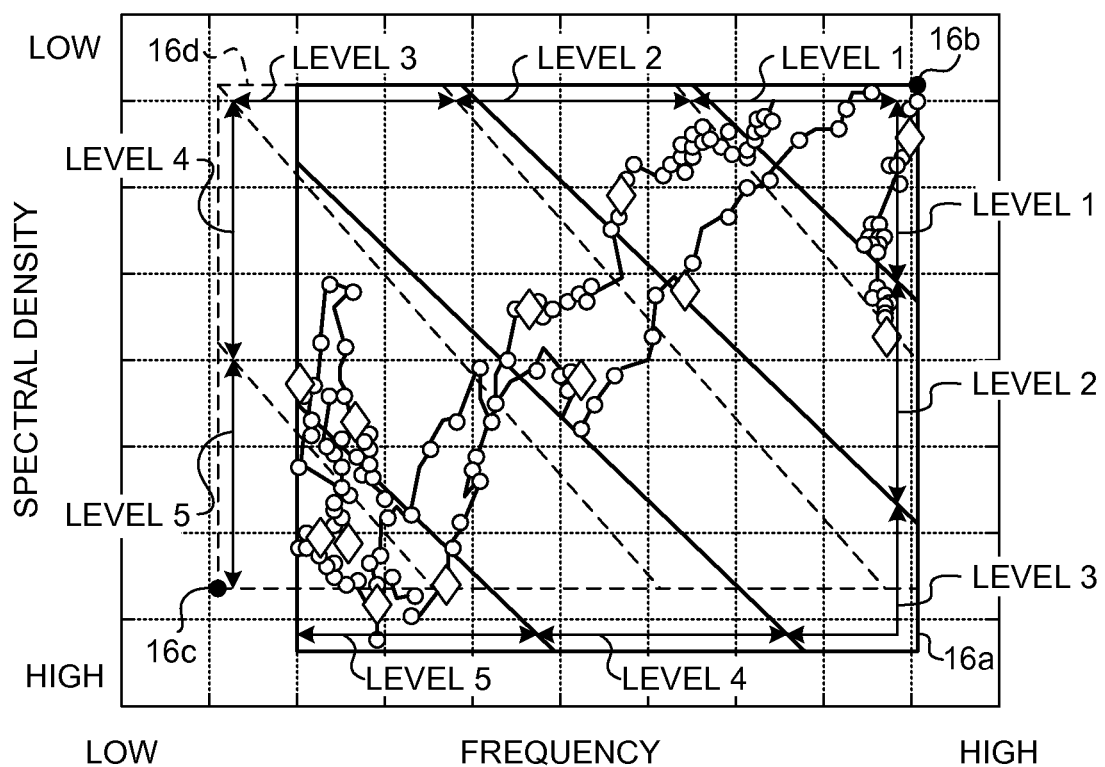
FIG. 16 is a schematic diagram illustrating an effect of using the wakefulness level determination unit according to the first embodiment.

FIG. 16 is a schematic diagram illustrating an effect of the wakefulness level determination unit according to the first embodiment. FIG. 16 illustrates an example of the result of experiments in which the heartbeat signal of a subject is obtained for more than one hour by using a driving simulator. The conventional technology sets a scale 16a by using this result of the experiment. In contrast, the wakefulness level determination unit 100 disclosed in the present invention estimates an estimation point 16c from a reference point 16b only by using the measurement results obtained during the few minutes after the start of experiments and sets a scale 16d. In this way, by obtaining the heartbeat signal only for the first few minutes after the start of the experiment, the wakefulness level determination unit 100 can easily set the scale 16d that is the same scale as that used in the conventional technology.

Furthermore, the wakefulness level determination unit 100 queries a subject about his/her current drowsiness level, thereby correcting a reference point in which the drowsiness level of a subject is "1". Accordingly, even if the wakefulness level determination unit 100 obtains the heartbeat signal of a subject in a state in which the subject is feeling drowsy, an estimation point is estimated by using the corrected reference point and thus a scale can be accurately set.

Furthermore, if the wakefulness level determination unit 100 obtains the maximum frequency and the maximum spectral density outside the scale that is previously set, the wakefulness level determination unit 100 extends the scale. Consequently, even if the calculated maximum frequency and the maximum spectral density are outside the scale, the extension unit 190 determines the calculated drowsiness level.

Furthermore, processing units, such as the calculating unit 120, the estimating unit 130, the setting unit 140, the determining unit 160, the receiving unit 170, the correction unit 180, and the extension unit 190, correspond to, for example, the following units. Specifically, the processing units correspond to an integrated circuit, such as an application specific integrated circuit (ASIC) or a field programmable gate array (FPGA). Furthermore, the processing units correspond to an electronic circuit, such as a central processing unit (CPU) or a micro processing unit (MPU).

Furthermore, the storing unit 150 corresponds to a semiconductor memory device, such as a random access memory (RAM), a read only memory (ROM), and a flash memory or corresponds to a storage device, such as a hard disk or an optical disk.

The configuration of the wakefulness level determination unit 100 illustrated in FIG. 1 is only an example. The wakefulness level determination unit 100 does not need all of the processing units illustrated in FIG. 1. For example, the wakefulness level determination unit 100 needs to only have a calculating unit, an estimating unit, a setting unit, and a determining unit.

Specifically, the calculating unit calculates a feature value from the heartbeat signal of a subject. On the basis of the correlation between a feature value of a subject when fully awake and a feature value of a subject when not fully awake, the estimating unit estimates a feature value of a subject when not fully awake from the feature value that is calculated by the calculating unit. The setting unit sets, as the index of the wakefulness level, the range from the feature value calculated by the calculating unit to the feature value estimated by the estimating unit. The determining unit compares the feature value calculated by the calculating unit with the index of the wakefulness level that is set by the setting unit, thus determining the wakefulness level of the subject.

[b] Second Embodiment

In the following, a description will be given of another embodiment of the wakefulness level determination unit, the wakefulness level determination method, and the wakefulness level determination program disclosed in the present invention.

In the first embodiment described above, a description has been given of a case in which the wakefulness level determination unit 100 determines the drowsiness level of a subject by using the maximum frequency and the maximum spectral density; however, the present invention is not limited thereto. Specifically, the wakefulness level determination unit 100 may also determine the drowsiness level of a subject by using only one of the maximum frequency and the maximum spectral density. For example, the wakefulness level determination unit 100 creates spectral density data on the basis of the heartbeat signal of a subject and then obtains the maximum point from the HF component of the created spectral density data. The wakefulness level determination unit 100 uses the correlation of the maximum frequency of the subject when fully awake and when not fully awake, thus estimating the maximum frequency of the subject when not fully awake from the obtained maximum frequency. The wakefulness level determination unit 100 divides the range, in which the maximum frequency vary from when the subject is fully awake to when the subject is not fully awake, into five, thus setting the index of a wakefulness level. The wakefulness level determination unit 100 compares the maximum frequency calculated from the heartbeat signal of the subject with the index of the wakefulness level, thus determining the wakefulness level of the subject.

Of the processes described in the first embodiment, the whole or a part of the processes that are mentioned as being automatically performed can also be manually performed, or the whole or a part of the processes that are mentioned as being manually performed can also be automatically performed using known methods. For example, a series of processes performed by the wakefulness level determination unit 100 illustrated in FIG. 15 may also be performed when an instruction is received from a driver after booting up a vehicle-mounted system that includes the wakefulness level determination unit 100 is booted up.

Furthermore, the flow of the processes, the control procedures, the specific names, and the information containing various kinds of data or parameters indicated in the above specification and drawings can be arbitrarily changed unless otherwise stated. For example, the data on the scale that is set by the setting unit 140 may also be constituted by both the frequency and the spectral density of the reference point and also the frequency and the spectral density of the estimation point. In such a case, because the storing unit 150 contains therein a value of each of the reference point and the estimation point, the determining unit 160 determines the drowsiness level of a subject after applying the normalized scale to the value of each of the reference point and the estimation point that are read from the storing unit 150 and resetting the scale.

Furthermore, the components of each unit in the wakefulness level determination unit 100 illustrated in FIG. 1 are only for conceptually illustrating the functions thereof and are not always physically configured as illustrated in the drawings. In other words, the specific shape of the separate or integrated wakefulness level determination unit 100 is not limited to the drawings. All or part of the wakefulness level determination unit 100 may be configured by functionally or physically separating or integrating any of the units depending on various loads or use conditions. For example, a server may also have some or all of the functions performed by the units, i.e., the calculating unit 120 to the extension unit 190, illustrated in FIG. 1. In such a case, the server and the wakefulness level determination unit 100 cooperate with each other via a network, and thereby the server may also determine the wakefulness level of a subject.

Furthermore, the wakefulness level determination unit 100 may also be implemented by having the functions performed by the units included in the wakefulness level determination unit 100 performed by a known information processing apparatus. The known information processing apparatus corresponds to a device, such as a personal computer, a workstation, a mobile phone, a personal handy-phone system (PHS) terminal, a mobile communication terminal or a personal digital assistant (PDA).

Figure 17:
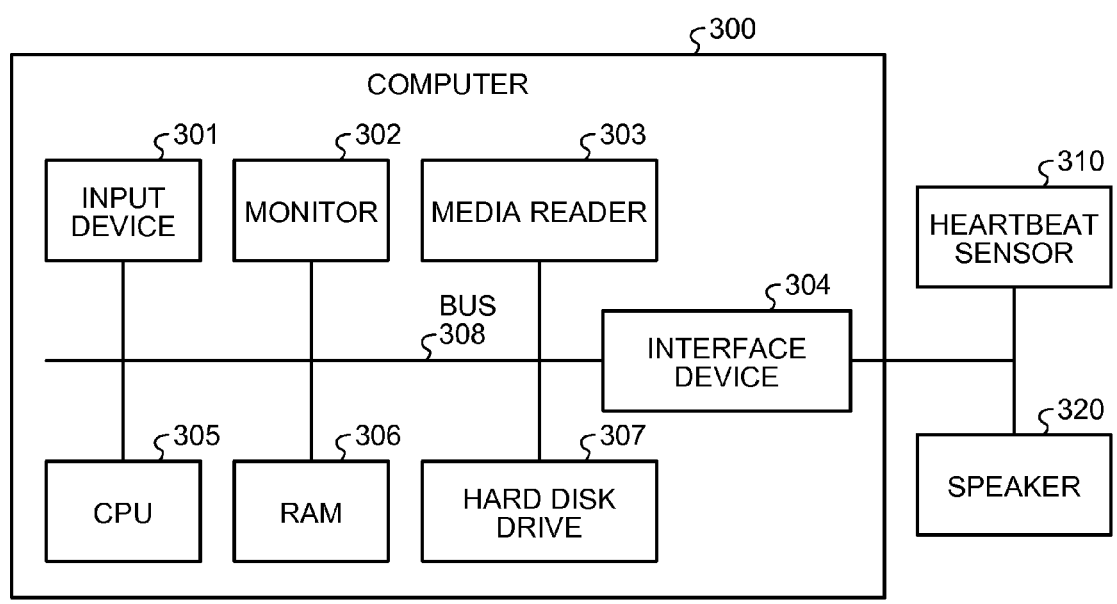
FIG. 17 is a block diagram illustrating a computer that executes a wakefulness level determination program according to the first embodiment.

FIG. 17 is a block diagram illustrating a computer that executes a wakefulness level determination program according to the first embodiment. As illustrated in FIG. 17, a computer 300 includes an input device 301 that receives data from a user, a monitor 302, a media reader 303 that reads a program or the like from a storage medium, and an interface device 304 that receives/transmits data between other devices. Furthermore, the computer 300 also includes a central processing unit (CPU) 305 that executes various kinds of arithmetic processing, a random access memory (RAM) 306 that temporarily stores therein various kinds of information, and a hard disk drive 307. Furthermore, each of the devices 301 to 307 is connected to a bus 308. Furthermore, the computer 300 is connected via the interface device 304 to a heartbeat sensor 310, which detects the heartbeat signal of a subject and a speaker 320.

The hard disk drive 307 stores therein various programs having the same functions as those performed by the processing units, such as the calculating unit 120, the estimating unit 130, the setting unit 140, the determining unit 160, the receiving unit 170, the correction unit 180, and the extension unit 190 illustrated in FIG. 1. Furthermore, the hard disk drive 307 stores therein the scale of a subject by associating the scale with the identification information that identifies the subject.

The CPU 305 reads the various programs from the hard disk drive 307 and loads them in the RAM 306, and thus the various programs function as various processes. Specifically, the various programs function as processes performed by the processing units, such as the calculating unit 120, the estimating unit 130, the setting unit 140, the determining unit 160, the receiving unit 170, the correction unit 180, and the extension unit 190.

The various programs described above are not always stored in the hard disk drive 307. For example, the computer 300 may also read and execute programs stored in a computer readable recording medium. Examples of the computer recording medium include a portable recording medium, such as a CD-ROM, a DVD disk, or a USB memory, a semiconductor memory, such as a flash memory, and a hard disk drive. Furthermore, the programs may also be stored in a device connected to, for example, a public circuit, the Internet, a local area network (LAN), a wide area network (WAN), or the like and the computer 300 may also read and execute the programs from the recording medium described above.

According to an aspect of the present invention, an advantage is provided in that it is possible to determine the wakefulness level of a subject.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A wakefulness level determination device comprising:
   a processor; and
   a memory coupled to the processor, wherein the processor executes a process comprising:
   detecting a heartbeat signal of a subject;
   calculating a first feature value from the heartbeat signal of the subject detected in a predetermined period of time during which the subject is assumed to be fully awake;
   estimating, from the first feature value, a second feature value representing a feature value of the subject when not fully awake, on the basis of a predetermined correlation between the first feature value and the second feature value;
   setting, as an index of a wakefulness level, a range from the first feature value to the second feature value;
   calculating a third feature value from another heartbeat signal of the subject; and
   determining a wakefulness level of the subject by comparing the third feature value with the index of the wakefulness level.

2. The wakefulness level determination device according to claim 1, wherein the process further comprises:
   receiving, from the subject, an instruction to correct the first feature value; and
   correcting, on the basis of the instruction received at the receiving, the first feature value that is used as a reference of the index, wherein
   the estimating includes estimating, on the basis of the correlation, the second feature value of the subject from the first feature value corrected at the correcting, and
   the setting includes setting, as the index of the wakefulness level, a range from the first feature value corrected at the correcting to the second feature value.

3. The wakefulness level determination device according to claim 1, wherein the process further comprises:
   extending the index of the wakefulness level when the third feature value is outside the range of the index of the wakefulness level, wherein
   the determining includes determining the wakefulness level of the subject by comparing the third feature value with the index of the wakefulness level extended at the extending.

4. A wakefulness level determination method executed by a computer, the method comprising:
   detecting a heartbeat signal of a subject;
   calculating, using a processor, a first feature value from the heartbeat signal of the subject detected in a predetermined period of time during which the subject is assumed to be fully awake;
   estimating, using the processor, from the first feature value, a second feature value representing a feature value of the subject when not fully awake, on the basis of a predetermined correlation between the first feature value and the second feature value;
   setting, using the processor, as an index of a wakefulness level, a range from the first feature value to the second feature value;
   calculating, using the processor, a third feature value from another heartbeat signal of the subject; and
   determining, using the processor, a wakefulness level of the subject by comparing the third feature value with the index of the wakefulness level.

5. The wakefulness level determination method according to claim 4, further comprising:
   receiving, using the processor, from the subject, an instruction to correct the first feature value; and
   correcting, using the processor, on the basis of the instruction received at the receiving, the first feature value that is used as a reference of the index, wherein
   the estimating includes estimating, on the basis of the correlation, the second feature value of the subject from the first feature value corrected at the correcting, and
   the setting includes setting, as the index of the wakefulness level, a range from the first feature value corrected at the correcting to the second feature value.

6. The wakefulness level determination method according to claim 4, further comprising:
   extending the index of the wakefulness level when the third feature value is outside the range of the index of the wakefulness level, wherein
   the determining includes determining the wakefulness level of the subject by comparing the third feature value with the index of the wakefulness level extended at the extending.

7. A non-transitory computer readable storage medium having stored therein a wakefulness level determination program causing a computer to execute a process comprising:
   detecting a heartbeat signal of a subject;
   calculating a first feature value from the heartbeat signal of the subject detected in a predetermined period of time during which the subject is assumed to be fully awake;
   estimating, from the first feature value, a second feature value representing a feature value of the subject when not fully awake, on the basis of a predetermined correlation between the first feature value and the second feature value;
   setting, as an index of a wakefulness level, a range from the first feature value to the second feature value;
   calculating a third feature value from another heartbeat signal of the subject; and
   determining a wakefulness level of the subject by comparing the third feature value with the index of the wakefulness level.

8. The non-transitory computer readable storage medium according to claim 7, the process further comprising:

receiving, from the subject, an instruction to correct the first feature value; and correcting, on the basis of the instruction received at the receiving, the first feature value that is used as a reference of the index, wherein the estimating includes estimating, on the basis of the correlation, the second feature value of the subject from the first feature value corrected at the correcting, and the setting includes setting, as the index of the wakefulness level, a range from the first feature value corrected at the correcting to the second feature value.

9. The non-transitory computer readable storage medium according to claim 7, the process further comprising:

extending the index of the wakefulness level when the third feature value is outside the range of the index of the wakefulness level, wherein the determining includes determining the wakefulness level of the subject by comparing the third feature value with the index of the wakefulness level extended at the extending.

* * * * *